(12) United States Patent
Yoshimura et al.

(10) Patent No.: US 7,662,626 B2
(45) Date of Patent: Feb. 16, 2010

(54) CELLS AND METHODS FOR ESTIMATION OF EFFECTS ON NEUROLOGICAL DYSFUNCTION

(75) Inventors: Seiko Yoshimura, Tokyo (JP); Eiichi Akahoshi, Kawasaki (JP); Mitsuko Ishihara, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 46 days.

(21) Appl. No.: 12/143,202

(22) Filed: Jun. 20, 2008

(65) Prior Publication Data

US 2009/0061474 A1 Mar. 5, 2009

Related U.S. Application Data

(62) Division of application No. 11/442,314, filed on May 30, 2006, now Pat. No. 7,413,898.

(30) Foreign Application Priority Data

May 30, 2005 (JP) ............................ 2005-157528

(51) Int. Cl.
C12N 5/00 (2006.01)
C12N 5/08 (2006.01)
C12N 5/10 (2006.01)
G01N 33/574 (2006.01)
C07H 21/02 (2006.01)

(52) U.S. Cl. ........................ 435/325; 435/368; 435/354; 435/7.23; 536/23.1

(58) Field of Classification Search ........................ None
See application file for complete search history.

(56) References Cited

U.S. PATENT DOCUMENTS 5,723,291 A 3/1998 Kushner et al.
6,762,029 B2 7/2004 Conley et al.

FOREIGN PATENT DOCUMENTS

JP 2004-305096 11/2004
JP 2004-305097 11/2004

OTHER PUBLICATIONS

Mark E. Hahn, "The aryl hydrocarbon receptor: A comparative perspective". Comparative Biochemistry and Physiology Part C 121 (1998) pp. 23-53.
Frank J. Gonzalez et al., "Anthony Y. H. Lu Commemorativve Issue: The Aryl Hydrocarbon Receptor", Drug Metabolism and Disposition vol. 26, No. 12, pp. 1194-1198, (1998).
Sandra L. Petersen, et al., "Distribution of mRNAs Encoding the Arylhydrocarbon Receptor, Arylhydrocarbon Receptor Nuclear Translocator, and Arylhydrocarbon Receptor Nuclear Translocator-2 in the Rat Brain and Brainstem", The Journal of Comparartive Neurology, 427:428-439 (2000).
Richard S. Pollenz, et al., "Analysis of Aryl Hydrocarbon Receptor-Mediated Signaling during Physiological Hypoxia Reveals Lack of Competitive for the Aryl Hydrocarbon Nuclear Translocator Transcription Factor", Molecular Pharmacology, 56:1127-1137 (1999).
Mark Wormke, et al., "The Aryl Hydrocarbon Receptor Mediates Degradation of Estrogen Receptor a through Activation of Proteasomes", Molecular and Cellular Biology 23(6), Mar. 2003, p. 1843-1855.
Tomohiro Ito, et al., "Constitutively Active Arylhydrocarbon Receptor Induces Growth Inhibition of Jurkat T. Cells through Changes in the Expression of Genes Related to Apoptosis and Cell Cylce Arrest", The Jounal of Biological Chemistry, vol. 279, No. 24, (2004), pp. 25204-25210.
G. Bartolini, et al., "Effect of a New Derivative of Rretinoic Acid on Proliferation and Differentiation in Human Neuroblatoma Cells", Anticancer Reseach 23: 1495-1500 (2003).
Celine Alleaume, et al., "Vasoactive intestinal peptide-induced neurite remodeling in human neuroblastoma SN-SY5Y cells implicates the Cdc42 GTPase and is independent of Ras-ERK pathway". Experimental Cell Research 299 (2004), pp. 511-524.
J. Knops, et al., Overexpression of Tau in a Nonneuronal Cell Induces Long Cellular processes, The Journal of Cell Biology, vol. 114, No. 4, Aug. 1991, pp. 725-733.
Bruce M. Spiegelman, et al., Aggregation of Microtubule Initiation Sites Preceding Neurite Outgrowth in Mouse Neuroblastoma Cells, Cell, vol. 16, pp. 253-263 (1979).
Zhengui Xia, et al., "Calcium Influx Via the NMDA Receptor Induces Immediate Early Gene Transcription by a Map Kinese/ERK-Dependent Mechanism", The Journal of Neuroscience, Sep. 1, 1996, 16(17):5425-5436.
Jiang et al., Gene Therapy 11: 1303-1311, 2004.
Jaworski et al,. J. Neurosc Res 60: 754-760, 2000.
Ghosh et al., Mol Biol Rep 27: 113-121, 2000.
Ema et al., Biochem Biophys Res Comm 184: 246-253, 1992.
Williamson et al., Tox Sc 83: 340-348, published online Nov. 2004.
Chen et al., J. Biol Chem 280: 4350-4359, 2005.
Qin et al., Dev Biol 270: 64-75, 2004.

(Continued)

Primary Examiner—Jeffrey Stucker
Assistant Examiner—Aditi Dutt
(74) Attorney, Agent, or Firm—Oblon, Spivak, McClelland, Maier & Neustadt, L.L.P.

(57) ABSTRACT

The invention provides neuron-derived cells obtained by transfecting a receptor-expressing nucleic acid having an aryl hydrocarbon receptor gene, wherein outgrowth of neurites is not observed without adding a substance for the aryl hydrocarbon receptor, and outgrowth of neurites is observed by adding the substance for the aryl hydrocarbon receptor. The invention also provides a method for determining the presence of neurotoxicity of a test substance, a method for acquiring a marker for determining the presence of neurotoxicity of the test substance, a method for acquiring a marker for neurological dysfunction, and a method for determining the effect of the test substance on neurological dysfunction using such cells.

7 Claims, 4 Drawing Sheets

OTHER PUBLICATIONS

Shigeki Shimba, et al., "Overexpression of the Aryl Hydrocarbon Receptor (AhR) Accelerates the cell Proliferation of A549 Cells[1]", J. Biochem., vol. 132, No. 5, 2002, 1 front page, pp. 795-802.

Linda E. Hays, et al., "Evidence that GABAergic Neurons in the Preoptic Area of the Rat Brain Are Targets of 2,3,7,8-Tetrachlorodibenzo-p-dioxin during Development", Environmental Health Perspectives, vol. 110, No. 3, Jun. 2002, pp. 369-376.

Chun Yang, et al., "Regulatory Interaction Between Arylhydrocarbon Receptor and SIM1, Two Basic Helix-Loop-Helix PAS Proteins Involved in the Control of Food Intake", The Journal of Biological Chemistry, vol. 279, No. 10, Mar. 5, 2004, pp. 9306-9312.

Seiko Yoshimura, et al., "Exposure to 2,3,7,8-TCDD Induces Neurite Extension in Neuro-2a Cells Over-Exressing Aryl Hydrocarbon Receptor (AhR)(N2a-R Cells)", The Collection of the Summaries of the Search Reports at the 7th Environmental Hormones Academy, 2004, p. 129 (with English translation).

SEQUENCE LISTING

<160> NUMBER OF SEQ ID NOS: 12

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cccaagctta ccatgagcag cggcgccaac atca                                34

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccgctcgaga ggaatccgct gggtgtgata tcag            34

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccgtccatcc tggaaattcg aacc                        24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccttcttcat ccgttagcgg tctc                        24

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cccacagcac cacaagagat a                           21

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aagtaggagg cacaatgtc                              19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccacggtgta ctggttcact                             20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

-continued

```
ggcatagttc ctgagcttgt                                        20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gatactgcag ggcaagagg                                         19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
caggcaccca cttttctttc                                        20

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tccggagaac gaagcggcta cagc                                   24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgctgaggtg ccgtggagat gtgt                                   24
```

CELLS AND METHODS FOR ESTIMATION OF EFFECTS ON NEUROLOGICAL DYSFUNCTION

CROSS-REFERENCE TO RELATED APPLICATIONS

This application is based upon and claims the benefit of priority from prior Japanese Patent Application No. 2005-157528, filed May 30, 2005, and U.S. application Ser. No. 11/442,314, filed May 30, 2006, issued as U.S. Pat. No. 7,413,898, dated Aug. 19, 2008; the entire contents of which are incorporated herein by reference.

BACKGROUND OF THE INVENTION

1. Field of the Invention

The invention relates to neuroblastoma cells which were transfected with the recombinant expression plasmid containing aryl hydrocarbon receptor gene. The invention also relates to a method for determining the neurotoxicity of test substance through an aryl hydrocarbon receptor, and a method for obtaining a marker for determining neurotoxicity of the test substance.

2. Description of the Related Art

Neurological disorder such as attention deficit hyperactivity disorder (ADHD) and learning disorder (LD) are major social problems. In the United States of America, about 3 to 5% of children up to age 18 are estimated to suffer from ADHD (Diagnosis and Treatment of Attention Deficit Hyperactivity Disorder, NIH Consensus Statement 1998, Nov. 16-18; 16(2): 1-37); similarly, in Japan, about 3 to 5% of children up to age 18 are also estimated to suffer from ADHD. Accordingly, it is an urgent problem to develop diagnostics and treatments for such neurological dysfunction.

Neurotoxicity of endocrine disruptors has been recently suspected to be a cause of such neurological disorder. The endocrine disruptors exhibit various toxicity such as reproduction toxicity, immunotoxicity and neurotoxicity, and a part of toxicity is known to be expressed through aryl hydrocarbon receptors (AhR) mediated pathway. The aryl hydrocarbon receptor is binding to polycyclic aromatic hydrocarbons (PAHs), and is a transcription factor belonging to bHLH-family. It has been reported that a part of immunotoxicity and reproductive toxicity of the endocrine disrupter is expressed through a pathway mediated by the aryl hydrocarbon receptor (Frank, J. G. et al., Drug Metabolism and Dispositions (1998), 26: 1194-1198). The aryl hydrocarbon receptor is conjectured to be related to neurotoxicity since expression of the aryl hydrocarbon receptor has been detected in brain tissue (Peterson, S. L. et al., J. Comp. Neurol. (2000), 427(3): 428-439). Correlation of expression of neurological functions and developmental formation with gene expression by the aryl hydrocarbon receptor has been also suggested. However, specific genes i.e. marker genes based on activation of transcription by the aryl hydrocarbon receptor in the nervous system hardly ever been identified. Accordingly, it is desired to construct an in vitro culture system suitable for acquiring and analyzing marker genes by analyzing the effect of the aryl hydrocarbon receptor on the neurological function, in order to develop effective diagnostics and treatments for neurological dysfunction.

Appropriate cells should be selected for constructing such an in vitro culture system. First, the cells are required to express the aryl hydrocarbon receptor. It is also desirable to select cells derived from undifferentiated neural cells before differentiation, for example neuroblastoma cells, because the aryl hydrocarbon receptor is considered to act on the nervous developmental process.

Many in vitro culture systems related to the aryl hydrocarbon receptor have been reported. In vitro culture systems using cells for expressing the aryl hydrocarbon receptor, for example Hepa-1 cells derived from mouse hepatic cells and HepG2 cells derived from human hepatic cells (Pollenz, R. S. et al., Mol. Pharmacol. (1999), 56(6): 1127-1137) and MCF-7 cells derived from human breast cancer cells (Wormke M. et al., Mol. Cell Biol. (2003), 23(6): 1843-55), have been constructed, and are used in a wide variety of fields from basic researches to applications such as evaluation of toxicity of chemical substances. Alternatively, it is reported that cells exogenously expressing the aryl hydrocarbon receptor are prepared by transfecting the aryl hydrocarbon receptor gene into cells not expressing the receptor to construct an in vitro culture system. Jarkat cells derived from human leukocytes are included in these cells (Ito, T. et al., J. Biol. Chem. (2004), 279(24): 25204-25210). However, no in vitro systems using cells derived from undifferentiated neural cells have been constructed, and it has been difficult to analyze the effect of the aryl hydrocarbon receptor on the development of the nervous system.

Marker genes and proteins that exhibit changes of expression when the function of the undifferentiated neural cells is expressed have been isolated. Examples of them include tyrosine hydroxylase involved in biosynthesis of dopamine (Bartolini, G. et al., Anticancer Res. (2003), 23(2B): 1495-1499), Cdc42 gene involved in reconstruction of cytoskeleton molecules during formation and outgrowth of neurites (Alleaume, C. et al., Exp. Cell Res. (2004), 299(2): 511-24), and tau gene involved in synapse formation (Knops, J. et al., J. Cell Biol. (1991), 114(24): 725-733). Decision of expression of the neural function of the undifferentiated neural cells is possible by detecting the expression of these molecules. A distinctive change of morphology that neurite outgrowth is observed when the undifferentiated neural cells express their nerve function, or when the cells are differentiated. This means that outgrowth of the neurite serves as a marker for determining the presence of expression of the neural function (Spiegelman B M et al., Cell. (1979), 16(2): 253-263).

BRIEF SUMMARY OF THE INVENTION

Accordingly, the object of the invention is to provide cells required for constructing an in vitro culture system capable of analyzing the effect of an aryl hydrocarbon receptor on the development of neural systems.

The inventors have succeeded, through intensive studies for solving the aforementioned problems, in producing cells stably maintaining nucleic acids on chromosomes by transfecting receptor-expressing nucleic acids in which an aryl hydrocarbon receptor gene is integrated into neuroblastoma cells. In addition, the inventors have succeeded in selecting a specific cells from all the prepared cells, which do not exhibit neurite outgrowth when a ligand of the aryl hydrocarbon receptor is not added to the culture medium, and which exhibit neurite outgrowth when the ligand of the aryl hydrocarbon receptor is added to the culture medium.

The invention provides neuron-derived cells for estimating neurotoxicity obtained by transfecting receptor-expressing nucleic acids having an aryl hydrocarbon receptor gene, wherein the neuron-derived cells do not exhibit neurite outgrowth when a ligand of the aryl hydrocarbon receptor is not added to the culture medium, and exhibit neurite outgrowth when the ligand of the aryl hydrocarbon receptor is added to the culture medium.

The invention also provides a method for estimating the effect of a test substance on neurological dysfunction through an aryl hydrocarbon receptor, comprising: contacting neural cells with the test substance; and measuring a change in morphology of the cells.

The invention further provides the method as described above, wherein the morphological change of the cells is an increase of a proportion of a number of cells with neurites having a twofold length of a diameter of the each cells.

The invention also provides a method for determining the effect of a test substance on neurological dysfunction through the aryl hydrocarbon receptor, comprising: contacting the cells with the test substance; and measuring a change of the amount of expression of a marker gene or a marker protein.

The invention also provides the method as described above, wherein the marker is a change of the amount of expression of a TH gene, Cdc42 gene or tau gene, or a tau protein or TH protein.

The invention provides a method for acquiring a marker gene of neurological dysfunction through the aryl hydrocarbon receptor, the method comprising: comparing an amount of expression of a gene between cells cultured by adding a ligand of aryl hydrocarbon receptor and cells cultured by adding no ligand of aryl hydrocarbon receptor; and acquiring a gene exhibiting a different amount of expression between the two types of the cells as a marker gene.

The invention also provides a method for acquiring a marker protein of neurological dysfunction through the aryl hydrocarbon receptor, the method comprising: comparing an amount of expression of a protein between cells cultured by adding a ligand of aryl hydrocarbon receptor and cells cultured by adding no ligand of aryl hydrocarbon receptor; and acquiring a protein exhibiting a different amount expression between the two types of cells as a marker protein.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

DETAILED DESCRIPTION OF THE INVENTION

As described above, it has been found that transcriptional activity of an aryl hydrocarbon receptor is activated by adding ligand of aryl hydrocarbon receptor in neuroblastoma cells in which a receptor-expressing nucleic acid having an aryl hydrocarbon receptor gene has been transfected, and the phenotype of the cell is characterized in that formation of neurites is observed.

The cells of the invention may be produced, for example, by the steps of: transfecting a receptor-expressing nucleic acid having an aryl hydrocarbon receptor gene into the cells; and selecting stable cells having the nucleic acid inserted into a chromosome. Neuron-derived cells are used for producing the cells of the invention. The neuron-derived cells may be any cells derived from and/or related to the neuron. For example, cells derived from neuroblastoma may be used. While the neuroblastoma cells may be cells originated from any species, they may be Neuro2a cells derived from mouse neuroblastoma cells. Either cell strains that have been established or cells isolated from the neuroblastoma may be used for the neuroblastoma cells.

Cells and methods for preparing the cells will be described below with reference to the neuroblastoma cells of the invention. The cells of the invention can be prepared by the following procedure.

Introduction of the Aryl Hydrocarbon Receptor Gene into the Neuroblastoma Cells (a) Preparation of the Aryl Hydrocarbon Receptor Gene The aryl hydrocarbon receptor gene is prepared as follows. Since the sequence of the aryl hydrocarbon receptor gene has been known, the gene can be isolated using a polymerase chain reaction (PCR). Examples of nucleic acids available as templates for PCR include cDNA synthesized from RNA extracted from any cells, or commercially available cDNA. The aryl hydrocarbon receptor gene may be any genes derived from any species, and examples of the gene may be derived from mammals such as rat, human and mouse, from fish such as zebra fish and cyprinodont, and bird such as domestic fowl. The gene is preferably derived from mammals, particularly from humans. A naturally occurring aryl hydrocarbon receptor gene may be directly used, or a part of the gene may be artificially modified so long as the function of aryl hydrocarbon receptor proteins is not changed. For example, the gene includes a gene in which one or several bases in the aryl hydrocarbon gene are deleted, added or substituted. The gene may include a gene in which base sequences upstream of a translation initiation codon have been changed to a Kozak sequence.

(b) Preparation of Receptor-Expressing Nucleic Acid

The aryl hydrocarbon receptor gene is integrated into an expression nucleic acid. An example of the expression nucleic acid includes a plasmid having a replication origin and a drug resistant gene, which functions in suitable microorganisms. At least one drug resistant gene is preferably integrated into the expression nucleic acid. For example, the expression nucleic acid contains two drug resistant genes, one of which is a drug resistant gene for maintaining the expression nucleic acid in microorganisms and the other is required for selection of the cells transfected by the expression nucleic acid. Examples of the drug resistant gene include a zeocin resistant gene and a hygromycin resistant gene. Commercially available plasmids may be used for these genes.

For example, the receptor-expressing nucleic acid is constructed by assembling the aryl hydrocarbon receptor gene prepared in (a) into the expression nucleic acid having the features as described above at the downstream of the promoter so as to be able to express the nucleic acid. Examples of the promoter include promoters that direct constructive expression, such as early phase or later phase promoters of a cytomegalovirus (CMV) promoter, Rous sarcoma virus (RSV) and simian virus (SV40). An inductive promoter such as a tetracycline responsive promoter may be also used. The promoter may be pre-integrated into the expression nucleic acid, or may be integrated into an appropriate site after inserting the aryl hydrocarbon receptor gene.

The aryl hydrocarbon receptor gene may be integrated into the expression nucleic acid as a naturally occurring nucleic acid, or may be integrated so as to be expressed as a tagged fusion protein. Isolation or detection of the protein may be facilitated by using the tagged protein. Examples of tags include a hystidine tag and V5 tag.

The constructed receptor-expressing nucleic acid is desirably confirmed that no mutation is introduced into the gene by sequencing at least a part of the aryl hydrocarbon receptor gene.

(c) Transfection of Expression Nucleic Acid into Neuroblastoma Cells

The receptor-expressing nucleic acid prepared in (b) above is transfected into the neuroblastoma cells. For example, at first, the cells are plated on a culture vessel, and are incubated in a culture medium in which Dulbecco's medium and Ham's F12 medium are mixed in an equal ratio (DF1:1) and contains 10% fetal bovine serum. The receptor-expressing nucleic acid is then transfected into the cells cultured as described above. Examples of the methods available for transfecting the receptor-expressing nucleic acid into the cell include those well known in the art such as a Lipofectamin, an electroporation, a DEAE-dextran and a calcium phosphate. For example, when Lipofectamin 2000 (manufactured by Invitrogen Co.) is used, the amount of the receptor-expressing nucleic acid to be introduced, the amount of Lipofectamin 2000, and the number of the cells are preferably determined in advance according to the instructions of a commercially available manual. The receptor-expressing nucleic acid may be introduced into the cell after modifying the nucleic acid into a linear nucleic acid by digesting with an appropriate restriction enzyme.

After transfecting the receptor-expressing nucleic acid into the cell, they are incubated for about 1 to 2 days. The cells are detached from the culture vessel, and are subcultured in a new vessel. Screening of cell lines using appropriate agents starts 1 or 2 day after the passage depending on the drug resistant gene integrated into the receptor-expressing nucleic acid. An appropriate concentration of the agent for screening is previously determined by a preliminary experiment depending on cell species used. A concentration of the agent by which 80 to 95% of the cells become extinct is usually appropriate as the concentration of the agent for screening. Culture is continued until drug resistant colonies derived from the cell line into which the receptor-expressing nucleic acid is transfected, grow into an appropriate size, while the culture medium is replaced once or twice every week with a fresh culture medium containing an appropriate concentration of the agent. Since the receptor-expressing nucleic acid is inserted into the chromosome and only the cells stably maintaining the receptor-expressing nucleic acid is allowed to proliferate, cells containing the receptor-expressing nucleic acid may be obtained.

(d) Selection of cells

Cells satisfying all the conditions (1) to (3) are selected from the cells obtained in (c) above. The order of the selection is arbitrary, and may start from any of the selections.

(1) Cells that stably maintain the receptor-expressing nucleic acid are selected from the cells obtained in (c). For confirming that the cell maintains the receptor-expressing nucleic acid, the aryl hydrocarbon receptor gene may be confirmed to be inserted into the genome of the cell. Insertion of the nucleic acid may be confirmed by a known DNA detection method such as Southern hybridization, a known RNA detection method by which transcripts of mRNA from the aryl hydrocarbon receptor gene on the transfected receptor-expressing nucleic acid are detected by northern hybridization or reverse transcription PCR, or a known protein detection method by which the aryl hydrocarbon receptor protein translated from the transfected receptor-expressing nucleic acid is detected by western blotting using an antibody specific to the aryl hydrocarbon receptor protein. When the aryl hydrocarbon receptor protein is expressed as a protein having a tagged sequence, the expression may be confirmed by a western blotting using an antibody specific to the tag sequence. Cells in which the aryl hydrocarbon receptor gene is detected by these conformation methods are used.

(2) Cells functionally expressed the aryl hydrocarbon receptor protein are selected from the cells obtained in (c). A gene known to be able to induce expression of the gene through activation of the aryl hydrocarbon receptor is used as a marker as an indication of the selection. Examples of the gene include genes for CYP1A1, UGT glycosyltransferase 1 family, polypeptide A6 (UGT1A6) or glutathione-S-transferase (GST). The selection procedure includes, for example, culturing the cells to be selected in a conventional culture medium such as DF1:1 medium containing 10% of fetal bovine serum for 1 to 5 days; culturing the cells in a conventional culture medium such as DF1:1 medium containing 10% of fetal bovine serum for 1 week by adding a ligand of aryl hydrocarbon receptor; and extracting RNAs from the cells to detect the expression of the marker gene by a known RNA detection method such as northern hybridization and reverse transcription PCR. Alternatively, the protein translated from the marker gene is detected by a known detection method such as western blotting. The cells confirmed to induce the expression of the marker gene by this confirmation are selected.

(3) Cells in which neurites outgrow this observed by adding ligand of the aryl hydrocarbon receptor, are selected from the cell strains obtained in (c). Cells into which the receptor-expressing nucleic acid is transfected are cultured in a conventional culture medium such as DF1:1 medium containing 10% fetal bovine serum with or without adding ligand of the aryl hydrocarbon receptor for 1 to 3 weeks. And morphological changes are compared between the two types of the cells described above. The number of the neurite from the cell, the length of the neurite, and the number of the cells in which the neurite is outgrown are compared when the morphology changes of the cell strain are used as indications. It is more preferable that comparison of increase of a proportion of a number of cells with neurite having a twofold length of a diameter of the each cells, to the total cells which are in contacted with a ligand of aryl hydrocarbon receptor. The cells in which the neurite is outgrown by adding ligand of the aryl hydrocarbon receptor are selected, by comparing the cells in which the receptor-expressing nucleic acid is transfected by adding the ligand of the aryl hydrocarbon receptor with the cells in which the receptor-expressing nucleic acid is transfected without adding the ligand of the aryl hydrocarbon receptor. While all the cells are not required to have the neurite in a single cell group, it is preferable that the proportion of the cells having the neurites is larger (see the photograph at the right side in FIG. 2).

The neuroblastoma cells obtained by the procedure above are called as cells responsive to neurotoxicity of the test substance (abbreviated as neurotoxicity-responsive cells hereinafter). Regulation of transcription through the aryl hydrocarbon receptor is activated by adding ligand of the aryl hydrocarbon receptor in the neurotoxicity-responsive cells. This means that transcription is activated through the aryl hydrocarbon receptor when the test substance is added. Accordingly, analysis of the gene or protein activated by the test substance is possible in the cell cultured by adding the test substance by comparing the cell with the cell cultured without adding the test substance (see FIG. 2). Consequently, the gene that serves as a marker gene or marker protein involved in neurological dysfunction may be provided by analyzing the neurotoxicity-responsive cells activated by adding the ligand of the aryl hydrocarbon receptor. Examples of neurological dysfunction include attention deficit hyperactivity disorder or learning disorder (LD), recognition disorder and Parkinson syndrome.

The method for determining the effect of the test substance on neurological dysfunction through the aryl hydrocarbon receptor will be described hereinafter.

(e) Screening of Neurotoxicity of Test Substance

The test substance is allowed to be contacted with the neurotoxicity-responsive cells. For example, the neurotoxicity-responsive cells are cultured in a culture medium in which the test substance is added and in a culture medium in which no test substance is added, respectively, for testing the effect of contact with the test substance. The cells are compared after cultivating the cells in these two mediums for an appropriate period. Morphological changes may be used as indication of the change of the cells. Otherwise, changes of expression of the gene or protein such as expression of the neurological function, outgrowth of the neurite and formation of synapse may be used as the marker.

An example of the morphological change of the cell is a structural change of cell frames. Specifically, the morphological change of a cell strain may be compared by the number of the neurite outgrowth of the cell, the length of the neurite, and the number of the cells exhibiting outgrowth of the neurite. It is preferable as an indication to use a proportion of a number of cells with neurites having a twofold length of a diameter of the each cells, to the total cells which are in contact with the test substance. When the number of the cells having neurite outgrowth is increased in the neurotoxicity-responsive cells cultured in a culture medium in which the test substance is added as compared with the neurotoxicity-responsive cells cultured in a culture medium without adding the test substance, the test substance may be determined to have an effect for enhancing transcriptional regulation through the aryl hydrocarbon receptor, or an effect for enhancing neurological dysfunction. The morphological change may be observed using any methods known in the art such as microscopic observation.

The change also includes the change of expression of neural marker genes such as TH gene or Cdc42 gene, or the change of expression of proteins such as TH protein and tau protein. When the amount of expression of the TH gene and Cdc42 gene is increased in the neurotoxicity-responsive cells cultured in a culture medium in which the test article is added as compared with the neurotoxicity-responsive cells cultured in a culture medium without adding the test substance, the test substance may be determined to have an effect for enhancing transcriptional regulation through the aryl hydrocarbon receptor, or an effect for enhancing neurological dysfunction. Neurotoxicity in the test substance may be likewise screened using the marker protein for neurological dysfunction. The change of expression as described above may be screened by any methods known in the art as described above.

The effect of toxicity by the endocrine disrupter, for example the substance that enhances neurological dysfunction, may be readily screened by using the method of the invention.

The method for acquiring the marker gene or marker protein of neurological dysfunction using the cell selected by the procedure described above will be hereinafter described.

The neurotoxicity-responsive cell selected by the method as described above is used in the method of the invention. For example, cells with accession numbers FERM BP-10341 and FERM BP-10342 may be used. As described above, transcriptional regulation through the aryl hydrocarbon receptor of these cells is activated in the presence of a substance having a binding ability to the aryl hydrocarbon receptor such as dioxin.

(f) Acquisition of Neurotoxicity Marker Gene

RNAs are extracted from the cells inserted with an aryl hydrocarbon receptor gene which is exposed to endocrine disruptors such as dioxin, for example PAHs and 2,3,7,8-TCDD, binding to the aryl hydrocarbon receptor. Likewise, RNAs are also extracted from the same cells not exposed to the endocrine disruptors. Then, genes differentially expressed between both RNAs are founded by any methods capable of comparing the amount of expression of RNAs. Any methods known in the art may be used for finding the genes. For example, a subtraction method, differential display method or a DNA chip may be used.

Neurotoxicity marker genes may be obtained from RNAs having a high level expression only in the toxicity responsive cells exposed to the endocrine disrupter. Contrary, it may be obtained from RNAs representing a low level or no expression in the toxicity responsive cells. The gene thus obtained may be considered to be involved in neurological dysfunction caused by the endocrine disruptors related to the aryl hydrocarbon receptor wherein transactivation is caused by binding of the endocrine disruptors to the aryl hydrocarbon receptor. The TH gene, Cdc42 gene and tau gene may be obtained from RNAs exhibiting a high level expression from only the toxicity-responsive cells exposed to the substance for the aryl hydrocarbon receptor.

The marker gene may be readily obtained by exposing the neuroblastoma cells to the test substance using the method according to the invention.

(g) Acquisition of Neurotoxicity Marker Protein

Proteins are extracted from the cells inserted with the aryl hydrocarbon receptor-expressing gene which is exposed to the endocrine disruptors binding to the aryl hydrocarbon receptor. Likewise, Proteins are also extracted from the same cells not exposed to the endocrine disruptors. Then, proteins having a different amount of expression are founded between the both types of proteins by any methods capable of comparing the amount of expression of the protein. Any methods known in the art, for example two-dimensional electrophoresis and protein chips, may be used for comparing the amount of expression of proteins.

Neurological dysfunction marker proteins may be obtained from the protein having a high level expression only in the neurotoxicity-responsive cells exposed to the ligand of the aryl hydrocarbon receptor. Contrary, it may be obtained from the protein having a low level or non-expression. The protein thus obtained is assumed to be involved in neurological dysfunction caused by the endocrine disruptors related to the aryl hydrocarbon receptor. The TH protein and tau protein may be obtained as the proteins having a high level expression only by the neurotoxicity-responsive cells exposed to the substance for the aryl hydrocarbon receptor.

The marker protein may be readily obtained by exposing the neuroblastoma cell to the test substance using the method according to the invention.

Expression of neurotoxicity through the aryl hydrocarbon receptor may be screened by using the marker and the neurotoxicity-responsive cells.

EXAMPLE 1

Preparation of Aryl Hydrocarbon Receptor Gene

Total RNAs were extracted from the brain of a rat using RNeasy kit (manufactured by Qiagen K.K.). The extracted RNA was reverse-transcribed using an oligo(dT) primer. A coding region of the rat aryl hydrocarbon receptor gene was amplified by 25 cycles of PCR comprising a cycle with denaturation of 94° C./1 minute, annealing of 55° C./1 minute and extension of 72° C./4 minutes using Pyrobest DNA polymerase and the reverse-transcripted RNAs as templates. A forward primer 5'-CCCAAgCTTACCATGAgCAgCggCgC-CAACATCA (SEQ ID NO: 1) and a reverse primer 5'-CCgCTCgAgAggAATCCgCTgggTgTgATATCAg (SEQ ID NO: 2) were used as primers. A HindIII restriction site was added at 5'-terminal of the forward primer, and a XhoI restriction site was added at 5'-terminal of the reverse primer. In addition, the reverse primer was designed so that the aryl hydrocarbon receptor protein is expressed as a fusion protein to which V5 epitope and hystidine tag are added.

EXAMPLE 2

Preparation of Receptor-Expressing Nucleic Acid in which Aryl Hydrocarbon Receptor Gene is Inserted pcDNA4/V5-His B (manufactured by Invitrogen Co.) was used for the expression nucleic acid. A multi-cloning site (MCS) is placed between the cytomegalovirus (CMV) promoter sequence and V5 epitope sequence in this pcDNA4/V5-His B. A desired protein can be over-expressed under the regulation of the CMV promoter by integrating a sequence encoding a desired gene at an appropriate restriction enzyme site within MCS.

Figure 1:
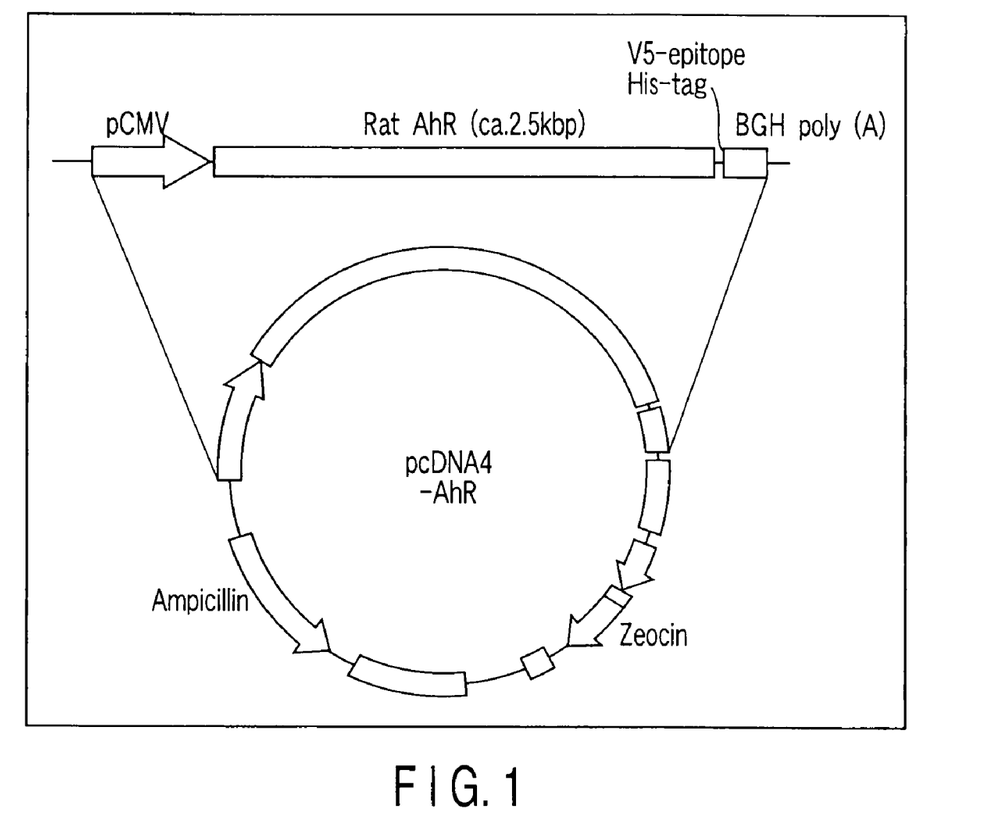
FIG. 1 is a construction diagram of the receptor-expressing nucleic acid in which the aryl hydrocarbon receptor gene is integrated.

It is also possible to add the V5 epitope and hystidine tag at the C-terminal of the desired protein by appropriately modifying the 3'-terminal of the coding sequence of the gene to be inserted. The coding region of the rat aryl hydrocarbon receptor gene of the expression nucleic acid amplified in Example 1 is digested with restriction enzymes HindIII and XhoI. pcDNA4/V5-His B was also digested with HindIII and XhoI. Then, expression nucleic acid pcDNA4-rAhR was prepared by ligating pcDNA4/V5-His B to the coding region of the rat aryl hydrocarbon receptor gene (FIG. 1). pcDNA4-rAhR was amplified and maintained in *E. coli* TOP10 (manufactured by Invitrogen Co.).

It was confirmed that no mutation was introduced into the region in pcDNA4-rAhR by sequencing the coding region of the rat aryl hydrocarbon receptor gene. T7 primer and BGH reverse primer were used for the sequencing primers.

EXAMPLE 3

Preparation of Neuro2a Derived from the Neuroblastoma into which Aryl Hydrocarbon Receptor-Expressing Nucleic Acid pcDNA4-rAhR is Transfected Lipofectamin 2000 (manufactured by Invitrogen Co.) was used to transfect aryl hydrocarbon receptor-expressing nucleic acid pcDNA4-rAhR into Neuro2a. Neuro2a was subcultured to 80% confluence ($2 \times 10^5$ cells) in a 24-well plate and then cultured in DF medium overnight. Mixed 50 µl of Opti-MEM medium (manufactured by Gibco Co.) with 2 µl of lipofectamin 2000, and the mixture incubated at room temperature for 15 minutes. The mixture was mixed with 50 µl of Opti-MEM medium containing 0.8 µg of receptor-expressing nucleic acid pcDNA4-rAhR prepared in Example 2. pcDNA4-rAhR was used after being digestion with MunI. A mixed solution of lipofectamin 2000 and receptor expressing nucleic acid was incubated at room temperature for 20 minutes, and was gently mixed by adding to Neuro2a that had been cultured in a 24-well plate. After culturing for 24 hours, Neuro2a was diluted to a concentration of 1/50 with fresh DF medium to subcultivate in a 6-well plate with additional incubation. After 24 hours, Zeocin (manufactured by Invitrogen Co.) was added to the medium at a concentration of 300 µg/ml, and selection of cells in which pcDNA4-rAhR was introduced was started. Culture was continued thereafter by replacing the medium with a fresh medium containing 300 µg/ml of Zeocin every 3 to 4 days. After 2 weeks, 76 colonies of Zeocin resistant cells were obtained using a cloning ring (manufactured by Iwaki Co., Ltd.). These cells were selected as a cell strain for stably maintaining receptor expressing nucleic acid pcDNA4-rAhR.

EXAMPLE 4

Selection of Cell Strain in Which Outgrowth of Neurite is Observed Under Conditions Exposed to 2,3,7,8-TCDD 76 species of the cell strain obtained in Example 3 were cultured in DF1:1 medium for 3 to 5 days, and cell morphology of each strain was observed. The cells were observed with an inverted microscope. The cell strains in which neurite outgrowth was not founded were selected. Although Neuro2a derived from neuroblastoma cells as a parent strain was cultured under the same conditions and observed with the microscope, few cells outgrowing the neurite were observed.

Figure 2:
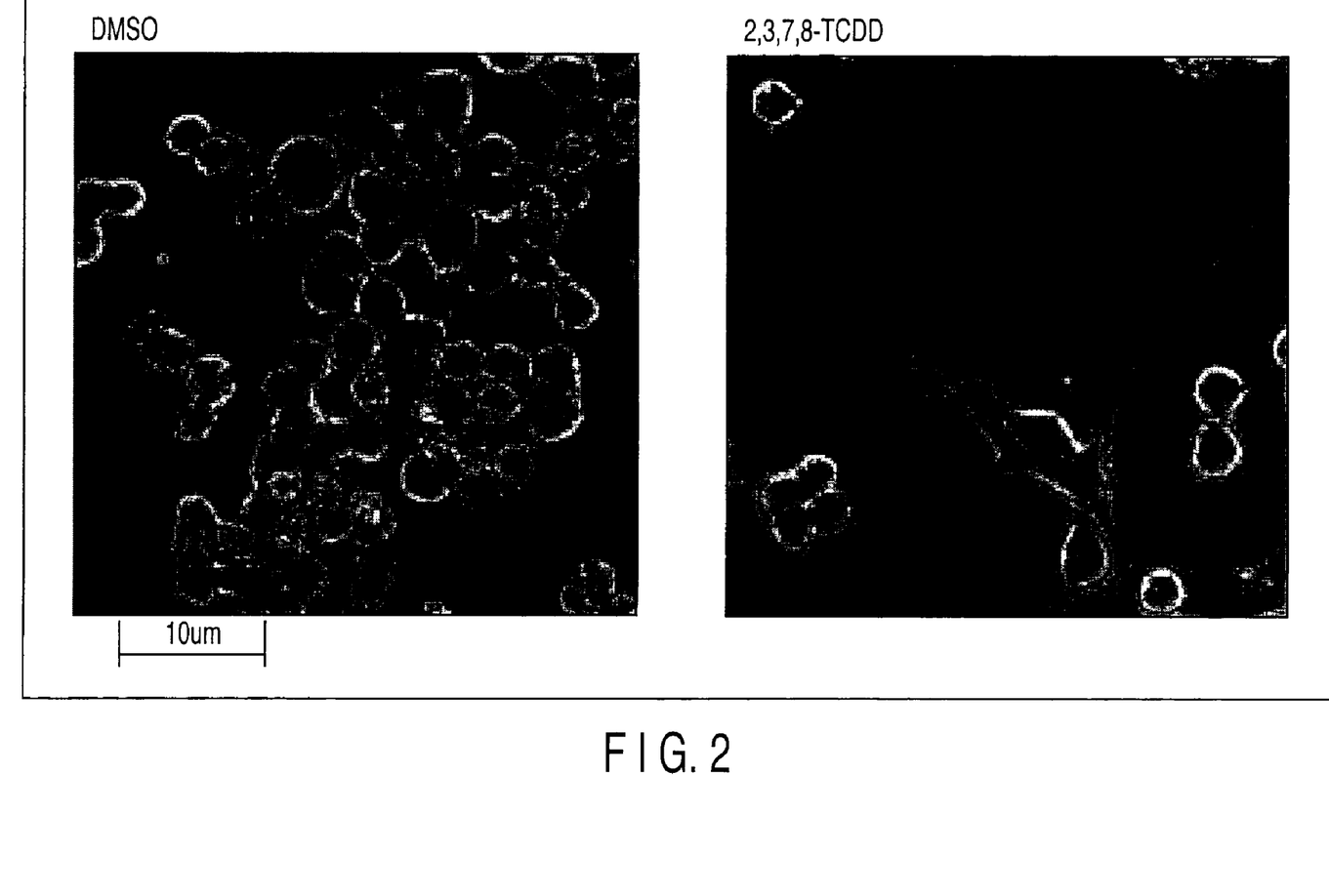
FIG. 2 shows microscopic photographs of a normal form of cells that responds to neurotoxicity of a test substance having no neuritis outgrowth, and a changed form of cells that responds to neurotoxicity of a test substance having neurites outgrowth by adding 2,3,7,8-TCDD(2,3,7,8-tetrachlorod-ibenzo-p-dioxin)

The selected cell strain was further cultured in DF1:1 medium supplemented with 10 nM of 2,3,7,8-TCDD for 1 to 3 weeks. Two cell strains having a particularly high proportion of neurite outgrowth were selected by observing the morphology of the cell (FIG. 2).

EXAMPLE 5

Expression of Marker Gene of Cell Strain in which Neurite Outgrowth are Observed Under Conditions Exposed to 2,3,7,8-TCDD Total RNAs were extracted from the two strains of the cell using RNeasy kit (manufactured by Qiagen K.K.). The extracted RNA was reverse-transcripted using an oligo(dT) primer. The receptor gene was amplified by 25 cycles of PCR comprising a cycle with denaturation of 94° C./30 seconds, annealing of 55° C./30 seconds and extension of 72° C./30 seconds using ExTaq polymerase (manufactured by Takara Bio Inc.) and reverse-transcripted DNA as a template. Then, mRNA transcripted from the aryl hydrocarbon receptor was amplified. A forward primer 5'-CCgTCCATCCTggAAAT-TCgAACC (SEQ ID NO: 3) and a reverse primer 5'-CCT-TCTTCATCCgTTAgCggTCTC (SEQ ID NO: 4) were used as PCR primers. As a result, the aryl hydrocarbon receptor gene was also detected in both cell strains selected. While the same experiment was performed with respect to Neuro2a, no aryl hydrocarbon receptor gene could be detected.

After cultivating these cell strains in DF1:1 suppremented with or without 30 nM of 2,3,7,8-TCDD for 24 hours, total RNAs were extracted from the cells. An RNeasy kit was used for extraction of total RNA. The extracted RNA was reverse-transcripted using an oligo(dT) primer. Subsequently, expression of CYP1A1 gene was confirmed by 25 cycles of PCR comprising 1 cycle with denaturation of 94° C./30 second, annealing of 55° C./30 seconds and extension of 72° C./30 seconds. CYP1A1 gene is one of genes, of which expression thereof is induced by binding of the aryl hydrocarbon receptor activated by binding of a ligand to XRE (xenobiotic responsive element) on DNAs. A forward primer 5'-CCCACAg-CACCACAAgAgATA (SEQ ID NO: 5) and a reverse primer 5'-AAgTAggAggCACAATgTC (SEQ ID NO: 6) were used as primers for PCR. As a result, expression of CYP1A1 gene was increased by adding 2,3,7,8-TCDD in both of two selected cell strains. While the same experiment was performed with respect to Neuro2a, no increase of the amount of expression of CYP1A1 gene was observed.

Figure 3:
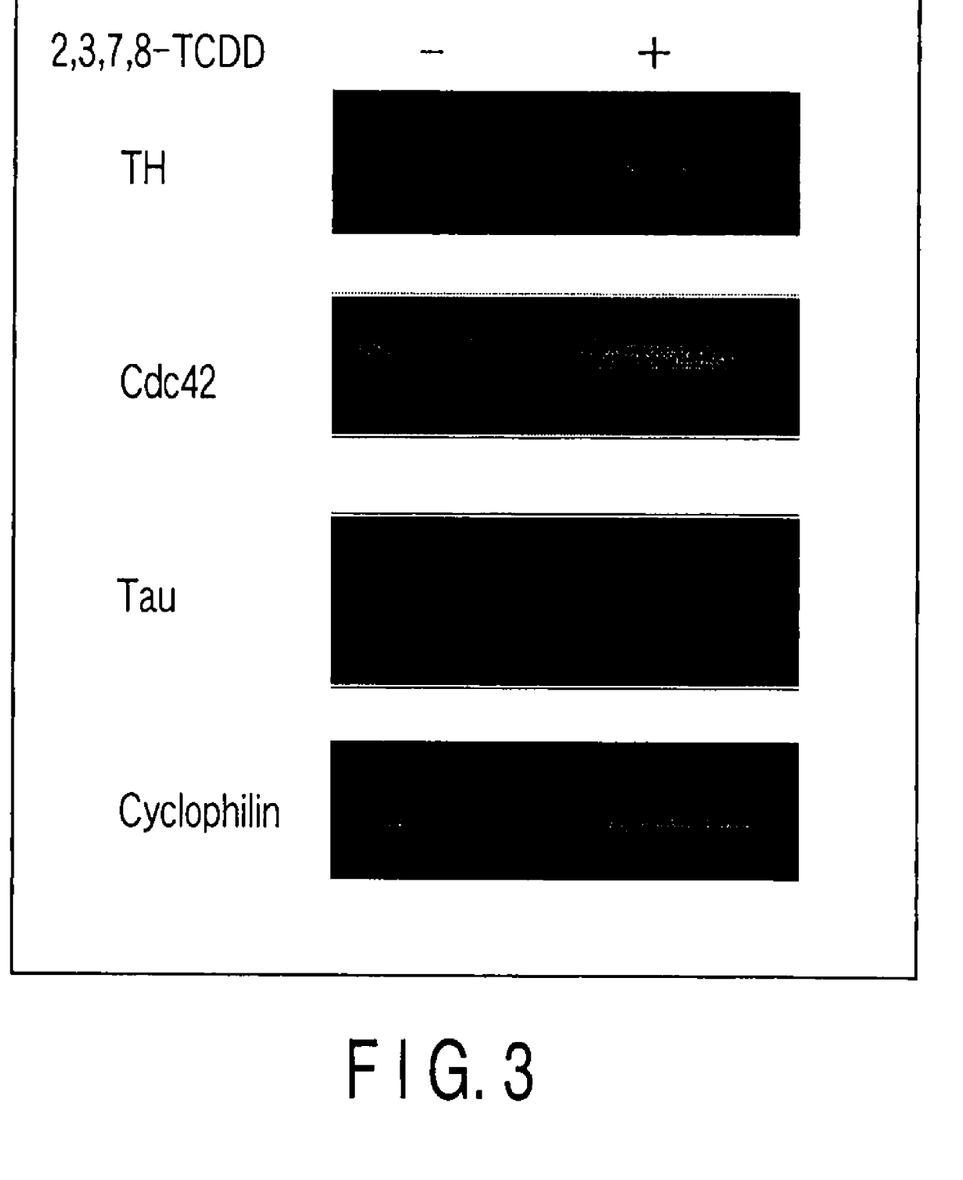
FIG. 3 shows electrophoresis photographs showing the changes of the amount of expression of TH genes, Cdc42 genes and tau genes.

Total RNAs were extracted with an RNeasy kit after culturing the selected two cell strains in DF1:1 medium supplemented with 2,3,7,8-TCDD, and cDNA was synthesized by a reverse transcription reaction. Subsequently, using cDNA synthesized above as a template and ExTaq (manufactured by Takara Bio Inc.), expression of the TH gene was confirmed by 25 cycles of PCR comprising one cycle with denaturation of 94° C./30 second, annealing of 60° C./30 seconds and extension of 72° C./30 seconds. Also, expression of the Cdc42 gene and tau gene was confirmed by 25 cycles of PCR comprising one cycle with denaturation of 94° C./30 second, annealing of 58° C./30 seconds and extension of 72° C./30 seconds. A forward primer 5'-CCACggTgTACTggTTCACT (SEQ ID NO: 7) and a reverse primer 5'-ggCATAgTTCCTgAgCTTgT (SEQ ID NO: 8) were used as primers for the TH gene; a forward primer 5'-gATACTgCAgggCAAgAgg (SEQ ID NO: 9) and a reverse primer 5'-CAggCACCCACTTTTCTTTC (SEQ ID NO: 10) were used as primers for the Cdc42 gene; and a forward primer 5'-TCCggAgAACgAAgCggCTA-CAgC (SEQ ID NO: 11) and a reverse primer 5'-TgCTgAg-gTgCCgTggAgATgTgT (SEQ ID NO: 12) were used as primers for the tau gene. As a result, the amounts of expression of the TH gene, Cdc42 gene and tau gene were increased in any of the two selected cell strains cultured with 2,3,7,8-TCDD as compared with the cell strains cultured without 2,3,7,8-TCDD (FIG. 3).

EXAMPLE 6

Figure 4:
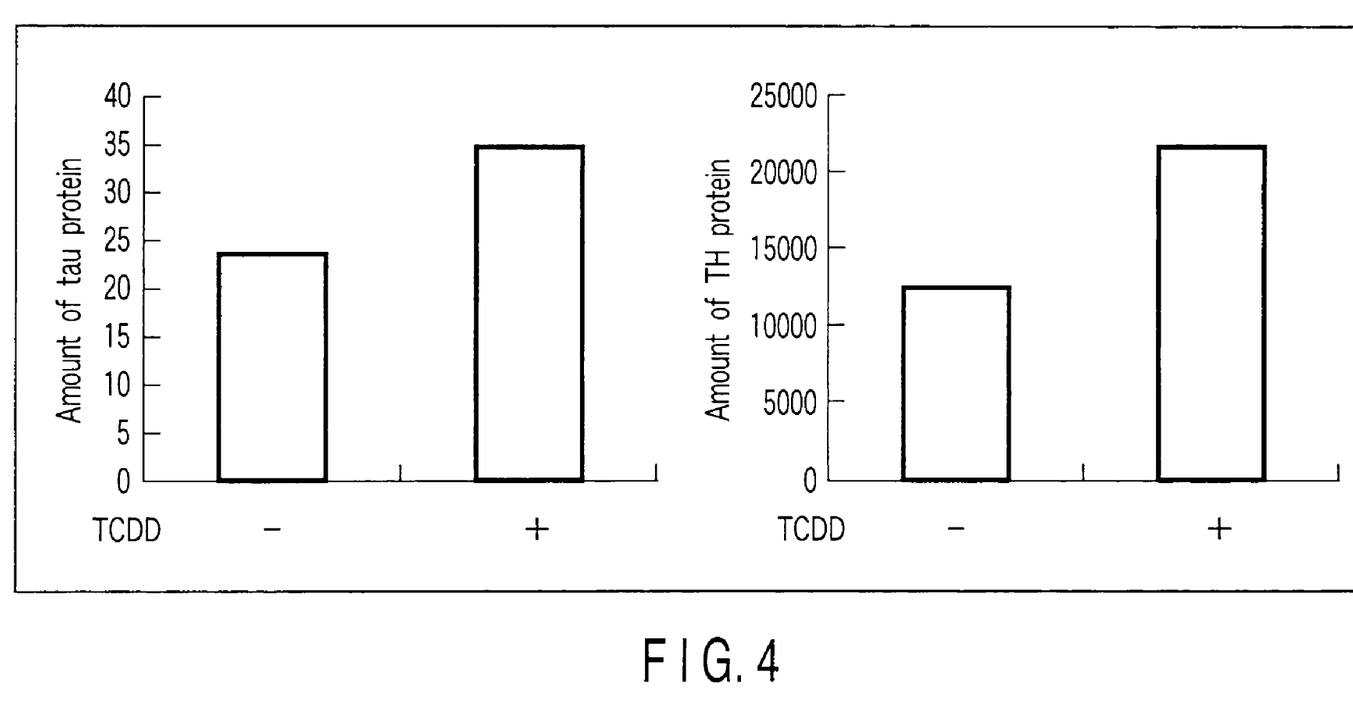
FIG. 4 shows graphs of the amounts of expression of the tau protein and TH protein, respectively, when 2,3,7,8-TCDD is added to the cells that respond to neurotoxicity of the test substance and when 2,3,7,8-TCDD is not added to the cells cultured by adding, respectively.

Expression of Marker Protein of Cell Strain in which Neurite Outgrowth is Observed Under Conditions Exposed to 2,3,7,8-TCDD After the selected two cell strains were cultured in DF1:1 medium supplemented with 10 nM of 2,3,7,8-TCDD for three weeks, the amounts of expression of the tau protein and TH protein were confirmed by extracting the proteins and by conducting western blotting with a tau protein antibody and TH protein antibody. The amounts of expression of the tau protein and TH protein were increased in any of the selected two cell strains as compared with neurotoxicity responsive cells cultured without adding 2,3,7,8-TCDD (FIG. 4).

The two selected cell strains were deposited at the International Patent Organism Depository with accession numbers of FERM BP-10341 and FERM BP-10342.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for determining the presence of neurotoxicity of a test substance, the neurotoxicity being mediated through an aryl hydrocarbon receptor, the method comprising:
   contacting neuron-derived cells with the test substance, and
   measuring the morphological changes of the cells,
   wherein the neuron-derived cells are neuron-derived cells obtained by being transfected with an aryl hydrocarbon receptor nucleic acid, wherein outgrowth of neurites is not observed without adding the test substance for the aryl carbon hydrocarbon receptor, and outgrowth of neurites is observed by adding the test substance for the aryl hydrocarbon receptor, wherein the neuron-derived cells are deposited under an accession number selected from the group consisting of FERM BP-10341 and FERM BP-10342.

2. The method of claim 1, wherein the morphological change is an increase of a proportion of a number of cells with neurites having a two fold length of a diameter of the cells, to the total number of cells which are in contact with the test substance.

3. The method according to claim 2, wherein the neuron-derived cells are neuroblastoma cells.

4. The method of claim 1, wherein the neuron-derived cells are neuroblastoma cells.

5. The method of claim 1, wherein the neuron-derived cells are Neuro2a cells.

6. The method of claim 1, wherein the neuron-derived cells are cells deposited under an accession number of FERMBP-10341.

7. The method of claim 1, wherein the neuron-derived cells are cells deposited under an accession number of FERMBP-10342.

* * * * *